(12) United States Patent
Pan et al.

(10) Patent No.: US 7,897,799 B2
(45) Date of Patent: Mar. 1, 2011

(54) OXO-HEXAMERIC ZIRCONIUM-OCTAAMINO ACID ANTIPERSPIRANT SALTS

(75) Inventors: Long Pan, Cherry Hill, NJ (US);
LaTonya Kilpatrick, Princeton, NJ (US); Xiaozhong Tang, Cherry Hill, NJ (US)

(73) Assignee: Colgate-Palmolive Company, New York, NY (US)

( * ) Notice: Subject to any disclaimer, the term of this patent is extended or adjusted under 35 U.S.C. 154(b) by 259 days.

(21) Appl. No.: 12/293,463

(22) PCT Filed: Sep. 12, 2008

(86) PCT No.: PCT/US2008/076105

§ 371 (c)(1),
(2), (4) Date: Sep. 18, 2008

(87) PCT Pub. No.: WO2009/039030

PCT Pub. Date: Mar. 26, 2009

(65) Prior Publication Data

US 2010/0234627 A1 Sep. 16, 2010

Related U.S. Application Data

(60) Provisional application No. 60/974,101, filed on Sep. 21, 2007.

(51) Int. Cl.
*C07F 7/00* (2006.01)
*A61Q 15/00* (2006.01)

(52) U.S. Cl. ............................... 556/56; 424/65; 424/66

(58) Field of Classification Search .................. 556/56; 424/65, 66
See application file for complete search history.

(56) References Cited

U.S. PATENT DOCUMENTS 4,223,010 A  9/1980  Rubino et al.

(Continued)

FOREIGN PATENT DOCUMENTS

EP  1 398 023 A  3/2004

(Continued)

OTHER PUBLICATIONS

Pan, Long et al., Synthesis and Structural Determination of a Hexanuclear Zirconium Glycine Compound Formed in Aqueous Solution, Inorganic Chemistry, vol. 47, No. 13, pp. 5537-5539, May 31, 2008.
International Search Report from PCT/US2008/076105, Dec. 19, 2008.

*Primary Examiner*—Porfirio Nazario Gonzalez
(74) *Attorney, Agent, or Firm*—Michael F. Morgan (57) ABSTRACT

A process for preparing oxo-hexameric zirconium-octaamino acid, such as glycine, salt comprising: mixing zirconium (Zr): amino acid:and mineral acid, in a molar ratio of 1:about 1 to about 15:about 1.5 to about 3 to form a mixture; filtering the mixture; and optionally, drying the mixture. An oxo-hexameric zirconium-octaamino acid salt of the molecular formula: oxo-$[Zr_6AminoAcid_8].Xy.nH_2O$, wherein Zr is zirconium, X is an anion of a mineral acid, and n and y are numerical values from 0 to 20. A method of making an antiperspirant active zirconium-aluminum-amino acid compound comprising mixing an oxo-hexameric zirconium-octaamino acid salt with aluminum chlorohydrex and/or aluminum chloride, and drying the mixture. The smallest oxo-hexameric zirconium-octaamino acid salt of this invention provides stability, efficacy, and shelf life of zirconium-amino acid species for formulations in antiperspirant and/or deodorant compositions.

25 Claims, 7 Drawing Sheets

U.S. PATENT DOCUMENTS

| | | |
|---|---|---|
| 4,871,525 A | 10/1989 | Giovanniello et al. |
| 5,955,064 A | 9/1999 | Giovanniello et al. |
| 5,997,850 A | 12/1999 | Tang |
| 6,066,314 A | 5/2000 | Tang et al. |
| 6,375,937 B1 | 4/2002 | Chopra |
| 6,649,152 B2 | 11/2003 | Carrillo et al. |
| 7,060,258 B2 | 6/2006 | Li |

FOREIGN PATENT DOCUMENTS

| | | |
|---|---|---|
| EP | 1 464 329 A | 10/2004 |
| GB | 1 549 617 A | 8/1979 |
| WO | 2007004163 A | 1/2007 |

OXO-HEXAMERIC ZIRCONIUM-OCTAAMINO ACID ANTIPERSPIRANT SALTS

CROSS REFERENCE TO RELATED APPLICATIONS

This application claims priority to U.S. Provisional Patent Application Ser. No. 60/974,101, filed on 21 Sep. 2007, and PCT/US2008/76105, filed 12 Sep. 2008, which is incorporated herein by reference.

BACKGROUND OF THE INVENTION

A variety of art is available that describes various zirconium-aluminum-glycine salts and methods of making them. In a typical aluminum zirconium glycine (abbreviated herein as "ZAG", "ZAG complexes" or "AZG") antiperspirant active species, the zirconium species enhances the efficacy because of its higher charge/size ratio resulting in its tendency to undergo rapid hydrolysis. The efficacy of ZAG is mainly dependent on the zirconium size distribution; i.e., uniform and smaller zirconium species will significantly enhance efficacy because of zirconium's strong tendency to hydrolyze even at a lower pH range, (pH of greater than 0 to 3). Glycine as a gelation inhibitor has been extensively employed in antiperspirant salts to prevent the zirconium (Zr) from further gelling or precipitating, thereby enhancing efficacy. It has been clinically shown that, in general, the smaller the species, the higher the efficacy on sweat reduction.

A number of efforts have focused on (1) how to select the components of ZAG which affect the performance of these materials as antiperspirants and deodorants and (2) how to manipulate these components to obtain and maintain the presence of smaller types of these components. In this regard, however, no pure phase of Zirconium-Glycine salt (abbreviated herein as "ZG") has been isolated and reported.

BRIEF SUMMARY OF THE INVENTION

The present invention overcomes the problems and disadvantages associated with current antiperspirant active species (ZAG) that hydrolyze rapidly by providing a synthetic route of producing mall and stabilized oxo-hexameric zirconium-octaamino acid species, such as zirconium-glycine (ZG), with a greatly reduced tendency of forming higher molecular weight zirconium complexes.

The invention is based in part on the finding that the smallest oxo-hexameric zirconium-octaamino acid salt provides improved stability and efficacy of zirconium-amino acid species for formulations in antiperspirant and/or deodorant compositions to improve efficacy and to extend shelf life.

In one embodiment, the invention includes a process for preparing an oxo-hexameric zirconium-octaamino acid salt, the process includes:
a) mixing zirconium (Zr):amino acid:and mineral acid (MA) in a molar ratio of 1:about 1 to about 15:about 1.5 to about 3 to form a mixture;
b) optionally, filtering the mixture; and
c) optionally, drying the mixture.

In another embodiment, the oxo-hexameric zirconium-octaamino acid salt has a molecular formula: oxo-$[Zr_6AminoAcid_8] \cdot X_y \cdot nH_2O$, wherein "Zr" is zirconium, "X" is an anion of a mineral acid, and wherein n and y are numerical values from 0 to 20.

Figure 1A:
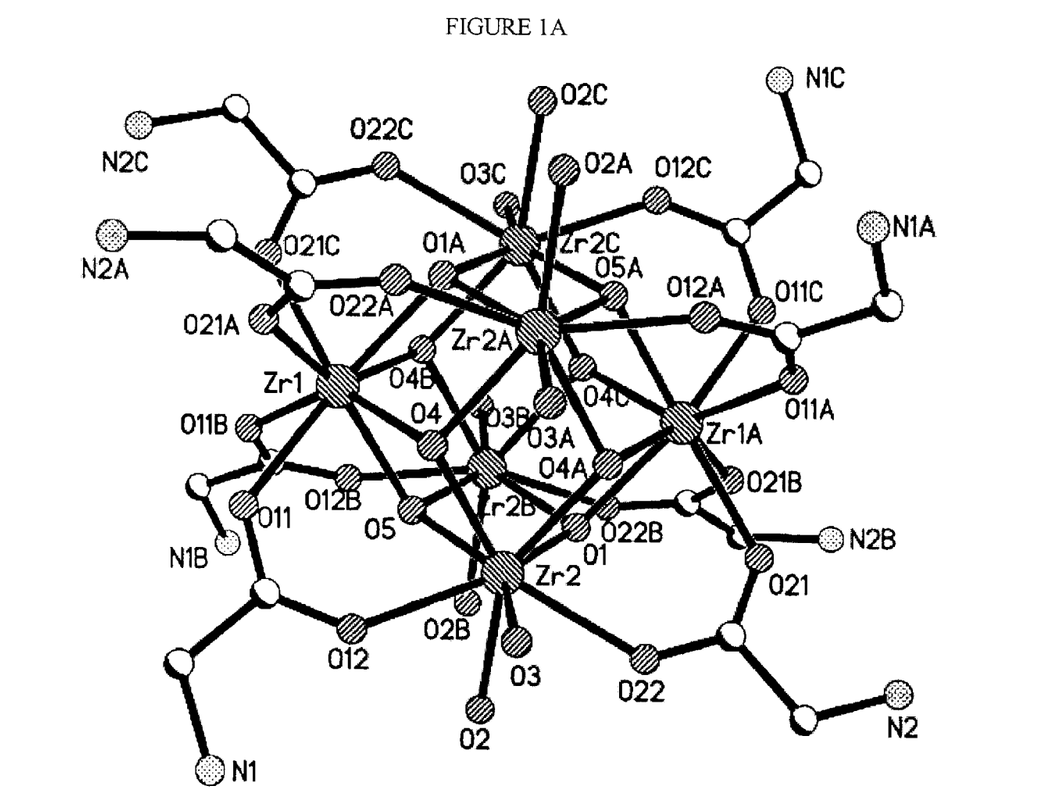
Figure 1B:
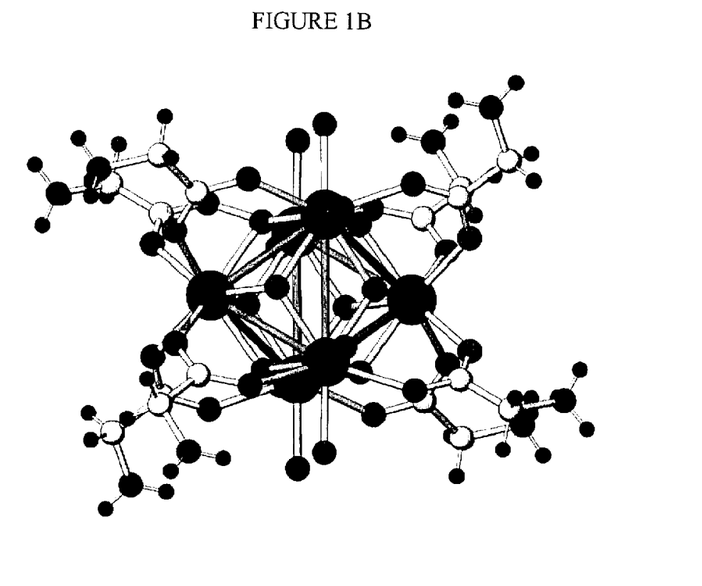
FIG. 1B is a stick structure with the hydrogen atoms shown.

In another embodiment, the oxo-hexameric zirconium-octaglycine cluster cation has a structure as shown in FIGS. 1A and 1B.

In another embodiment, a method of making an antiperspirant active zirconium-aluminum-amino acid compound comprising the steps of:
a) mixing an oxo-hexameric zirconium-octaamino acid salt in an aqueous solution;
b) admixing aluminum chlorohydrex (ACH) and/or aluminum chloride ($AlCl_3$) into the oxo-hexameric zirconium-octaamino acid salt solution to form a mixture; and
c) drying the mixture to obtain the zirconium-aluminum-amino acid salt;
wherein a molar ratio of zirconium-amino acid to ACH and/or $AlCl_3$ is 1:about 1.2 to about 1:5.

In further embodiments of the above embodiments, the amino acid is glycine.

BRIEF DESCRIPTION OF THE DRAWINGS

In order to facilitate a fuller understanding of the present disclosure, reference is now made to the accompanying drawings. These drawings should not be construed as limiting the present disclosure, but are intended to be exemplary only.

FIG. 1A is a structure of oxo-$Zr_6Gly_8$ cluster cation. The counterions and solvent molecules are omitted for clarity. The shading code is: zirconium (diagonal lines running from upper left to lower right); oxygen (diagonal lines running from lower left to upper right); nitrogen (checkerboard); carbon (half black and half white); and hydrogen atoms (not pictured) on the carbon and nitrogen atoms to complete the valence for each atom. There are four oxygen atoms (02, 02A, 02B, and 02C) shows with incomplete valences. These can be completed with hydrogen atoms or they can be bonded to another structure.

DETAILED DESCRIPTION OF THE INVENTION

Unless otherwise specified, all percentages and amounts expressed herein and elsewhere in the specification should be understood to refer to percentages by weight. Also, the term "about," when used in reference to a range of values, should be understood to refer to either value in the range, or to both values in the range. As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

The term antiperspirant is defined in 21 C.F.R. 350.3. As used herein the term "stabilized" is meant that the small zirconium-glycine complex formed with the glycine amino acid retains approximately the same amount of the smaller zirconium species present in the initial sample as evaluated by size exclusion chromatography "SEC" after at least 30 days aging at room temperature.

As used herein the term "mineral acid" is meant an acid derived from inorganic minerals by chemical reaction as opposed to organic acids. Examples include but are not limited to the following acids: hydrochloric acid, hydrobromic acid, nitric acid, phosphoric acid, sulfuric acid, boric acid, hydrofluoric acid, and perchloride. In another embodiment, the mineral acid is at least one acid chosen from $Cl^-$ or $SO_4^{2-}$ or $NO_3^-$.

The term "crystal" refers to a form of a solid state of matter, which is distinct from its amorphous solid state. Crystals display characteristic features including a lattice structure, characteristic shapes and optical properties such as refractive index. A crystal contains atoms arranged in a pattern that repeats periodically in three dimensions.

The present invention relates to stabilization of small oxo-hexameric-zirconium-octaamino acid salts and methods for forming them to formulate antiperspirant actives with enhanced efficacy.

Synthesis of Oxo-Hexameric Zirconium-OctaAmino Acid Salt

By virtue of the strong acidity resulting from charge/size ratios, zirconium possesses the remarkable tendency to undergo facile hydrolysis reactions. For example, U.S. Pat. Nos. 6,066,314 and 5,997,850 (Tang el al.) incorporated herein by reference, disclose various zirconium salts, aluminum salts and amino acids in the preparation of aluminum zirconium glycine (ZAG) antiperspirant active salts to stabilize small zirconium species in aqueous solution.

In one embodiment, a new synthetic route was employed involving low pH, higher ratio of amino acid: zirconium with an excess amount of concentrated mineral acid and extra stabilizer strategy (herein referred to as ECAES) to force the smallest hexameric zirconium-amino acid species to form without the species undergoing further hydrolysis reactions.

Exemplary zirconium compounds of this invention include zirconium oxy salts and zirconium hydroxy salts, also referred to as zirconyl salts and zirconyl hydroxy salts, and are represented by the general empirical formula $ZrO_m(OH)_n(H_2O)_1L_z$, wherein z varies from about 0.9 to about 2 and is not necessarily an integer; m or n is greater than or equal to 0; 1 is 0 to 20; and L is selected from halides, nitrate, sulfamate, sulfate, and mixtures thereof.

In certain embodiments, excess amino acid, such as glycine, is added to a zirconium component such as $ZrOCl_2$ and/or $ZrO(OH)Cl$, in ratios of at least 1:12 in a concentrated mineral acid such as hydrochloric acid or sulfuric acid or nitric acid at room temperature, stirred, and the solution evaporated and filtered before drying. The drying can be done at any temperature that results in drying of the mixture. In one embodiment, the drying temperature is room temperature or higher. The resulting solid may be purified by recrystallization methods or by fractionation on one or more solid chromatographic supports, alone or linked in tandem to isolate pure form of oxo-$Zr_6AminoAcid_8$ salt.

The zirconium complex often employs a compound with a carboxylate group for stabilization, and advantageously this is an amino acid. In one embodiment, glycine which has the formula $CH_2(NH_2)COOH$ is used as the suitable complexant to stabilize zirconium. In other embodiments, suitable amino acids other than glycine which may be added to the zirconium salts in the ratios described herein include but are not limited to alanine, threonine, leucine, tryptophan, phenylalanine, valine, and methionine. In certain embodiments the amino acids used are water soluble. In certain embodiments, mixtures of amino acids may also be used.

In an embodiment, the solutions and products made from the oxo-hexameric zirconium-octaamino acid salt exhibit increased stability of the small zirconium-amino acid species in aqueous environments, thus maintaining efficacy and increased shelf life of products such as antiperspirants and deodorants made therefrom.

In one embodiment the process for preparing an oxo-hexameric zirconium-octaamino acid salt of this invention involves:
a) mixing zirconium (Zr):amino acid:and mineral acid (MA) in a molar ratio of 1:1 to about 15:1.5 to 3 to form a mixture;
b) optionally, filtering the mixture; and
c) optionally, drying the mixture to isolate the oxo-hexameric zirconium-octaamino acid salt.

The mixing can be conducted at any temperature and with any type of mixer. For example, the mixing can be done at room temperature (about 23° C.).

In another embodiment, the molar ratio of zirconium (Zr): amino acid:mineral acid (MA) is 1:at least about 1, 2, 3, 4, 5, 6, 7, 8, 9, 10, 11, 12, 13, 14, or 15 to about 2, 3, 4, 5, 6, 7, 8, 9, 10, 11, 12, 13, 14, or 15:at least about 1.5, 2.0, or 2.5 to about 2.0, 2.5, or 3. In another embodiment, the molar ratio is in the range of 1:about 8 to about 12:about 1.5 to about 3. In another embodiment, the molar ratio is in the range of 1:about 9 to about 1.1:about 1.8 to about 2.2. In another embodiment, the molar ratio is 1:14.07:2.76. In another embodiment, the molar ratio is 1:about 10:about 2.

in an alternate embodiment of the process of preparing oxo-hexameric zirconium-octaamino acid salt of this invention, the molar quantities of amino acid and mineral acid (MA) are at least two times in excess of the molar quantity of zirconium to lead to a pure oxo-$Zr_6AminoAcid_8$ cluster after filtration. If the ratio is below this amount, the oxo-$Zr_6AminoAcid_8$ cluster will be present with other materials.

In an alternate embodiment of the method of preparing the oxo-hexameric zirconium-octaamino acid salt, the molar ratio of glycine to zirconium (Gly/Zr) is at least about 1.3.

Crystal Structure of Oxo-Hexameric Zirconium-OctaAmino Acid Salt

In certain embodiments of this invention, the oxo-hexamer zirconium-octaamino acid hexamer cluster salt of this invention is composed of a oxo-$Zr_6AminoAcid_8$ cationic complex balanced by an anion group, such as those mentioned above for the mineral acid, that will not only meet a desired efficacy zirconium species but also provide a clear structural environment of zirconium with amino acid. In another embodiment, the amino acid is glycine.

In another embodiment, the oxo-hexameric zirconium-octaamino acid salt has a molecular formula: oxo-$[Zr_6AminoAcid_8]$.$Xy$.$nH_2O$, wherein Zr is zirconium, X is an anion from an above listed mineral acid, such as $Cl^-$, $SO_4^{2-}$, $NO_3^-$, and wherein n and y are numerical values from 0 to 20. The above zirconium-amino acid salt may have coordinated and/or bound water in various quantities.

In an embodiment, the oxo-hexameric zirconium-octaglycine salt has a molecular formula: oxo-$[Zr_6Gly_8]$.$Xy$.$nH_2O$, wherein Zr is zirconium, Gly is glycine, X is an anion from an above listed mineral acid, such as $Cl^-$, $SO_4^{2-}$, $NO_3^-$, and wherein n and y are numerical values from 0 to 15. The above zirconium glycine salt may have coordinated and/or bound water in various quantities.

The crystal structure of oxo-$Zr_6Gly_8$ complex has been determined using single crystal X-ray diffraction (SXRD) method as shown in FIG. 1A. (e.g. $SO_4^{2-}$ as the anion: space group: C2/m; cell lengths: a=24.979(4)Å, b=11.4356(17)Å, c=13.725(2)Å; cell angles: α=90.00°, β=115.902(2)°, γ=90.00°; cell volume: 3526.7 Å$^3$)

In one embodiment, the crystalline oxo-hexameric zirconium-glycine salt has six zirconium atoms located in an octahedral molecular geometry; wherein each adjacent three zirconium (Zr) atoms are capped by eight oxygen atoms to form a $Zr_6O_8$ core; and wherein each Zr is connected by a carboxylic group of a glycine as syn-syn mode to an apical Zr atom in the octahedral geometry.

Powder X-Ray Diffraction (PXRD)

Powder X-Ray diffraction (PXRD) was used as a method to identify and characterize oxo-hexameric zirconium-octaglycine crystal. The powder X-ray diffraction pattern was determined using a Rogaku D/M-2200T automated diffraction system. The sample was prepared for analysis by packing the powder onto a glass wafer specimen mount. The specimen was rotated whilst being irradiated with copper K-alpha X-rays (wavelength (λ=1.5406 Angstroms) with the X-ray tube operated at 40 kV/40 mA. The analysis was performed with the goniometer running in step-scan mode set for a 5 second count per 0.02 step over a two theta range of 5° to 50°.

Figure 2:
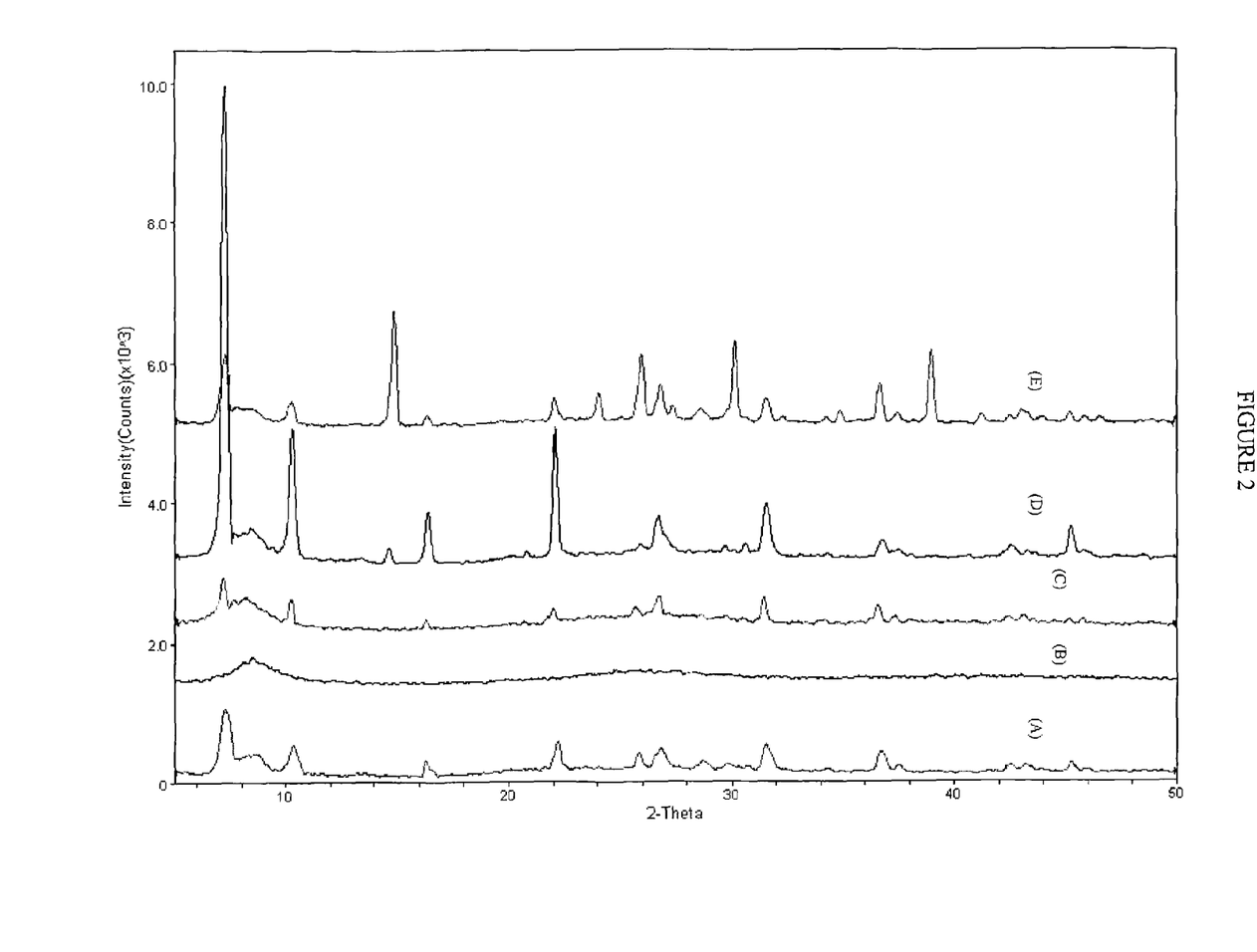
FIG. 2 is an X-ray powder diffraction structure obtained using copper K alpha radiation of: A) oxo-$Zr_6Gly_8$ crystal, B) SUMMIT™ Z576 (ZAG) (from Summit Research Labs, Huguenot, N.Y.) powder, C) physical mixture of oxo-$Zr_6Gly_8$ Crystal and SUMMIT™ Z576, D) oxo-$Zr_6Gly_8$ crystal and SUMMIT™ Z576 (ZAG) isolated from aqueous solution thereof; E) mixture of oxo-$Zr_6Gly_8$ crystal and $AlCl_3 \cdot 6H_2O$ isolated from aqueous solution thereof.

FIG. 2 shows that pure complexes of oxo-$Zr_6Gly_8$ have been obtained. This is the smallest hexameric zirconium-glycine crystal ever synthesized. As evident from FIG. 2, ZAG is an amorphous powder that does not display diffraction peaks. In contrast, the oxo-$Zr_6Gly_8$ species displays several sharp diffraction peaks that can be detected regardless of the type of mixture it is incorporated evidencing the crystalline nature of the salt.

The peak locations, "d"-spacings, and intensities of greater than 5% for oxo-$Zr_6Gly_8$ crystal (sample A) are summarized in Table 1. In Table 1, "Angle 2-θ" is related to the interplanar spacing "d values" of the crystal, and the intensity is given as a percentage of the greatest peak ($I/I_t$).

TABLE 1

XRPD data of sample oxo-$(Zr_6Gly_8)$ with $Cl^-$ as an anion

| Angle 2θ | d (Å) | $I/I_1$ |
|---|---|---|
| 7.37 | 11.98 | 100 |
| 7.95 | 11.10 | 30.33 |
| 8.77 | 10.08 | 70.72 |
| 10.43 | 8.47 | 50.38 |
| 10.85 | 8.15 | 10.99 |
| 16.53 | 5.36 | 9.93 |

As will be appreciated by the skilled crystallographer, the relative intensities of the various peaks within Table 1 may vary due to a number of factors such as for example orientation effects of crystals in the X-ray beam or the purity of the material being analyzed or the degree of crystallinity of the sample. The peak positions may also shift for variations in sample height but the peak positions will remain substantially as defined in Table 1.

The skilled crystallographer will also appreciate that measurements using a different wavelength will result in different shifts according to the Bragg equation "nλ=2d sin θ", where θ is the angle of incidence, λ is the wavelength of incident X-ray beam, "d" is the inter-planar spacing of the atomic layers in a crystal and n is an integer.

Such further PXRD patterns generated by use of alternative wavelengths are considered to be alternative representations of the PXRD pattern of the crystalline material of the present invention and as such are within the scope of the present invention.

Antiperspirant Formulations

The antiperspirant active oxo-hexameric zirconium-octaamino acid salt useful herein for the purpose of this invention include but are not limited to formulating antiperspirants having improved efficacy. Such antiperspirants include solids such as sticks and creams (creams sometimes being included in the term "soft solid"), gels, liquids (such as are suitable for roll-on products), and aerosols. The forms of these products may be suspensions or emulsions as described in U.S. Pat. No. 6,375,937 (Chopra et al.), which is incorporated herein by reference.

In one embodiment, the oxo-hexameric zirconium-octaamino acid salt is a precursor for synthesizing aluminum zirconium-amino acid, such as an aluminum zirconium glycine ("ZAG").

In one embodiment, a method of making an antiperspirant active Zirconium-Aluminum-amino acid, such as a ZAG, is provided, the method comprising the steps of:

a) mixing an oxo-hexameric zirconium-octaamino acid salt precursor in an aqueous solution;

admixing aluminum chlorohydrex (ACH) and/or aluminum chloride ($AlCl_3$) into the oxo-hexameric zirconium-octaamino acid hexamer solution to form a mixture; and c) drying the mixture to obtain the zirconium aluminum amino acid salt;

wherein a molar ratio of zirconium-amino acid to ACH and/or $AlCl_3$ is 1:about 1.2 to about 1:5. The oxo-hexameric zirconium-octaamino acid salt can be any of the oxo-hexameric zirconium-octaamino acid salts described herein.

The drying can be accomplished at any temperature that results in drying the mixture. In one embodiment, the drying is spray drying.

In another embodiment, antiperspirant product compositions according to the present invention contain the oxo-hexameric zirconium-octaamino acid salt in an amount about 0.01% to 30% by weight, of the total weight of the composition.

In another embodiment, the oxo-hexameric zirconium-octaamino acid salt can be mixed with aluminum chlorohydrate. The amount of each can be any desired amount. In one embodiment, the amounts are such that the molar ratio of aluminum:zirconium is 1-10:1-6. In certain embodiments, for FDA approved compositions, the amounts are such that the molar amount of aluminum:zirconium is 10:2, 10:6, or 6:2.

EXAMPLES

Exemplary embodiments of the present invention will be illustrated by reference to the following examples, which are included to exemplify, but not limit the scope of the present invention.

In the examples and elsewhere in the description of the invention, chemical symbols and terminology have their usual and customary meanings. Temperatures are in degrees Celsius unless otherwise indicated. "AP" means antiperspirant active, "gly" means glycine, "Zr" means zirconium, "ZG", means the oxo-$Zr_6Gly_8$ complex. The amounts of the components are in weight percents based on the standard described; if no other standard is described then the total weight of the composition as 100% is to be inferred. Various names of chemical components include those listed in the CTFA International Cosmetic Ingredient Dictionary (Cosmetics, Toiletry and Fragrance Association, Inc., 7$^{th}$ ed. 1997). The temperature is room temperature (about 20° C.).

After the filing of the priority application, the invention was described in a publication in Inorganic Chemistry, Vo. 47, No. 13, pp. 5537-5539, 31 May 2008, which is incorporated herein by reference. The following Example A was published in this publication.

Example A

Hydrated zirconium oxide chloride, glycine and sulfuric acid with a molar ratio of 1:14.07:2.76 were mixed in an aqueous solution at pH 2.52. Insoluble colorless column crystals were formed after several days. The crystals turned opaque and decayed due to the loss of solvent after being taken out of the mother liquor for a few minutes. For this reason a high quality crystal was sealed in a glass capillary together with the mother liquor for data collection. The IR spectrum showed two peaks at 1587 and 1460 cm$^{-1}$, which were assigned to $v_{as}$ COO$^-$ and $v_a$ COO$^-$, respectively. The structure of the title compound 1 (FIG. 1B), with formula $[Zr_6(OH^-)_8(H_2O)_8(Gly)_4(Gly^-)_4] \cdot (SO_4^{2-})_6 \cdot 14H_2O$, was determined by single crystal X-ray diffraction. Crystal data of compound 1; $[Zr_6(OH^-)_8(H_2O)_8(Gly)_4(Gly^-)_4](SO_4)_6 \cdot 14H_2O$. Mr=2252.62, monoclinic, space group C2/m, a=24.979(4), b=11.4356(17), c=13.725(2) Å, β=115.902(2)°, V=3526.7(9) Å$^3$, Z=2, $\rho_{calcd.}$=2.121 gcm$^{-3}$, μ(MoKα)=1.173 mm$^{-1}$, 13734 reflections measured, 3645 unique ($R_{int}$=0.040, 2θ$_{max}$=26°), 3101 with I≧2σ(I), 290 variables, 17 restrains, GOF=1.172, $R_1$=0.070, $\omega R_2$=0.171. Diffraction data were collected on a Bruker SMART CCD diffractometer with MoKα radiation (λ=0.71073 Å) at 203(2) K. The structure was solved by direct methods with SIR97 program and refined by full-matrix least-squares treatment again F$^2$ using the SHELXTL program suite. Absorption corrections were applied empirically using SADABS program. The hydrogen atoms were not added. CCDC-659843 contains the supplementary crystallographic data for this paper. The data can be obtained from The Cambridge Crystallographic Data Centre via www.ccdc.cam.ac.uk/data_request/cif. (considering the disorder, we also refined a non-disordered model in the supplementary material). This structure depicts a hexanuclear zirconium core $[Zr_6(OH)_8]^{12+}$ with $D_{4h}$ symmetry. The cluster is a slightly flattened octahedron. The zirconium atoms form the corners of the octahedron. The eight faces of the octahedron are capped by the $\mu_3$-OH$^-$ groups. In addition to these groups, there are four ligands attached to each octahedron corner. These four ligands at the apical corners are the oxygen atoms from the carboxylic groups of Gly, while at the equatorial corners only two are from the carboxylic groups. The remaining two are from H$_2$O with the Zr—O distances of 2.203-2.211 Å. The eight vertical edges of the flattened octahedron are bridged by the glycine ligands, whereas the four equatorial edges are not bridged. In the Zr$_6$ cluster; the Zr—Zr distances of 3.524-3.528 Å at the apical edges are slightly shorter than those of the Zr—Zr contacts of 3.549-3.554 Å in the equatorial plane. The eight $\mu_3$-OH— groups have similar coordination geometry compared to that of other $\mu_3$-OH— species reported in the literature. The bond distances of Zr(IV)—OH in the range of 2.146-2.194 Å are shorter than the those of Zr(IV) with the oxygen atoms of the bridging carboxylic groups (2.222-2.269 Å). The average bond angles of the $\mu_3$-OH$^-$ coordination (109.16°) are close to the tetrahedral angle of 109°, but smaller than that of $\mu_3$-O(>113°).

The four equatorial Zr(IV) corners are connected to the apical Zr(IV) ones by eight carboxylic groups of different glycine molecules in a syn-syn mode. The four Zr-centered polyhedra in the equatorial plane are connected to each other by sharing one edge, and they are connected to the apical Zr by sharing four edges. As is well known, glycine can exist as either a neutral (—OOC—CH2-NH$_3^+$) or an anion form (—OOC—CH$_2$—NH$_2$)$^-$. Both neutral and anion modes of amino acid can coexist in one structure to meet overall charge balance requirement. Two glycine molecules on left side at the upper half of the Zr$_6$ octahedron are assigned as neutral, while two on the other side are assigned as anionic. At the lower half of the octahedron, the assignment is reversed (FIG. 1B). These assignments are based on the C—C and C—N distances reported for neutral and anionic glycine. The C—C distance is slightly shorter, and the C—N distance slightly longer in the anionic form of glycine. Examination of the structure revealed that the C—C and C—N bond lengths of four glycines are 1.520 and 1.479 Å corresponding to —OOC—CH$_2$—NH$_3^+$ while those of the remaining four glycines are 1.520 and 1.470 Å corresponding to —OOC—CH$_2$—NH$_2$ respectively. The size of the hexanuclear cluster is ca. 13.4 Å. There are six sulfate ions in the unit cell as counter ions for charge balance and fourteen water molecules engaged in a number of hydrogen bonds in the structure.

Figure 3:
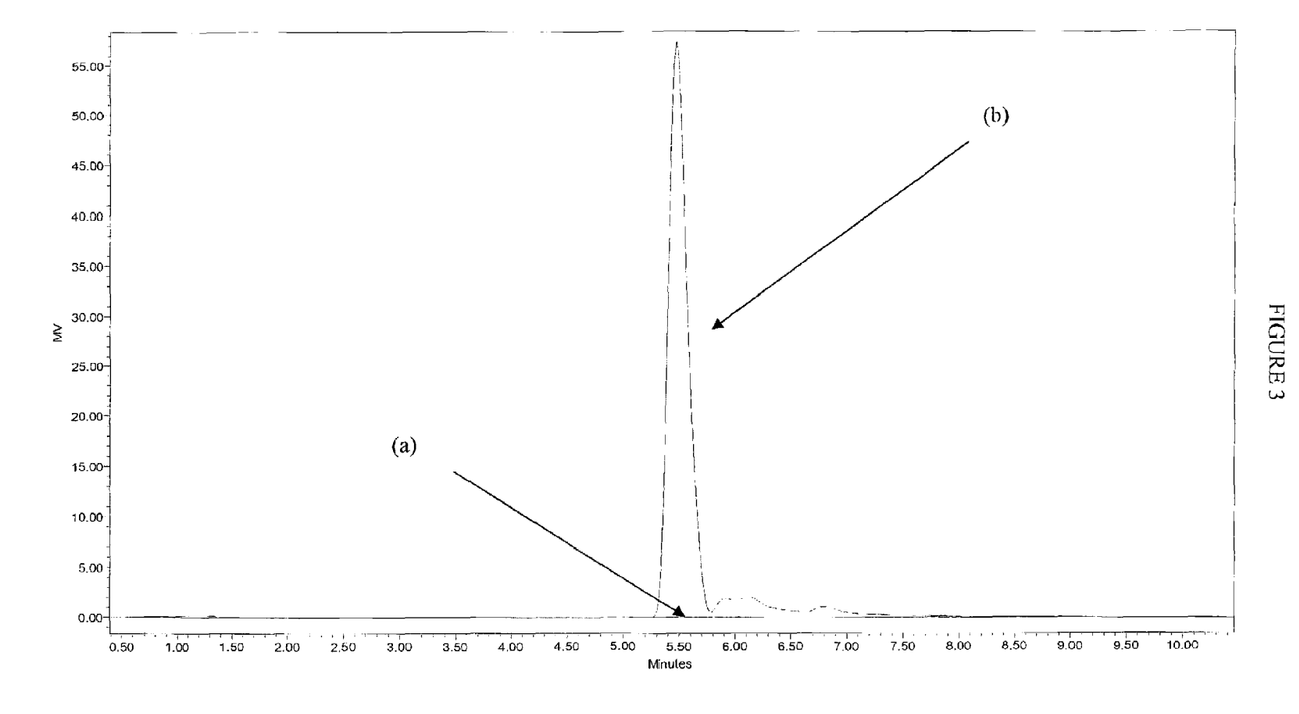
FIG. 3 is a SEC (a) and HPLC (b) chromatogram of a solution of oxo-$Zr_6Gly_8$.

The charge assignment is also consistent with our electronic structure calculations. It is well known that in a $M_6X_8$ ($M_6$ octahedron with all faces capped by X ligands) or $M_6X_{12}$ ($M_6$ octahedron with all edges bridged by X ligands) type cluster, there exist 11 (for $M_6X_8$) or 8 (for $M_6X_{12}$) M-M bonding and M-X nonbonding molecular orbitals. These orbitals can accommodate additional skeleton electrons: In the case of our compound, only one low-lying orbital of $a_{1g}$ symmetry is of M-M bonding. The others are high in energy due to additional terminal ligands (four on each Zr). This orbital, however, is of Zr—O antibonding character where the oxygen is the octahedron face-capping ligand. The Molecular Orbital Overlap Population (MOOP) diagram as calculated by the extended Hückel method is shown in FIG. 3. In this figure, the MOOP's calculated for the Zr—Zr and Zr—O (face-capping) bonds in the experimentally determined structure are plotted on the left and right half of the graph. The HOMO of pseudo $a_{1g}$ symmetry in the cluster of $D_{4h}$ point group is indeed of Zr—Zr bonding and Zr—O (face-capping) antibonding. The computational result reveals that the Zr$_6$ core should have no skeleton electron.

Example B

Synthesis of $[Zr_6(OH^-)_8(H_2O)_8(Gly)_4(Gly^-)_4] \cdot (SO_4^{2-})_6 \cdot 14H_2O$ (1): To a mixture of hydrated ZrOCl2.8H2O (0.322 g, 1 mmol), glycine (1.055 g, 14 mmol) and 4 mL of 15 MΩ water, sulfuric acid (98%) (0.15 mL) was slowly added to form a clear solution. After one week, colorless column crystals were formed and collected in solution. IR (4000-400 cm$^{-1}$); 3006(w), 2969(w), 2908(w), 2657(br), 2446(br), 2049 (br), 1627(sh), 1518(s, 1460(vs), 1419(s), 1415.9(vs), 1341 (vs), 1140(br), 1079(sh), 1029(c), 968(vs), 921(s), 687(sh), 649(s). EA analysis (Exp: Cal %): Zr(24.1; 24.30), C(8.76; 8.53), H(3.97; 3.94), N(4.94; 4.97), S(8.13; 8.54).

Example 1

Glycine powder is added to a zirconium compound (of a 31% solution of hydrate zirconium oxychloride ($ZrOCl_2$) with concentrated hydrochloric acid with stirring. The final solution will have a molar ratio of (Zr):glycine (Gly):mineral acid (MA) in a molar ratio of 1:10:2. The solution is filtered. The solution is stirred at room temperature (about 20° C. to 30° C.) until the solution is evaporated to dryness leaving a solid. The solid is purified by recrystallization to obtain pure form of oxo-$Zr_6Gly_8$ complex.

Example 2

Glycine powder is added to a zirconium compound (of a 31% solution of zirconium oxychloride ($ZrOCl_2$) admixed with concentrated sulfuric acid with stirring. The final solution will have a molar ratio of (Zr):glycine (Gly):mineral acid (MA) in a molar ratio of 1:10:2. The solution is filtered. The solution is stirred at room temperature (about 20° C. to 30° C.) until the solution is evaporated to dryness leaving a solid. The solid is purified by recrystallization to obtain pure form of oxo-$Zr_6Gly_8$ complex.

Example 3

Glycine powder is added to a zirconium compound (of a 31% solution of hydrated zirconium oxychloride ($ZrOCl_2$) admixed with concentrated Hydrochloric acid with stirring. The final solution will have a molar ratio of (Zr):glycine (Gly):mineral acid (MA) in a molar ratio of 1:10:2. The solution is stirred at room temperature until the solution is evaporated to isolate before drying to a solid. The solid is purified by recrystallization to obtain pure form of oxo-$Zr_6Gly_8$ complex.

Analytical Data for Examples 1-3

Size exclusion chromatography ("SEC") or gel permeation chromatography ("GPC") described in U.S. Pat. No. 6,066,314, incorporated herein by reference, illustrates the use of SEC as a routine method used for obtaining information on aluminum and zirconium polymeric species distribution in antiperspirant salt solutions. With appropriate chromatographic columns, at least five distinctive groups of polymer species can be detected in a ZAG antiperspirant, appearing in a chromatogram as peaks 1, 2, 3, 4 and a peak known as "5.6". Peak 1 is the larger Zr species (greater than 120-125 Å). Peaks 2 and 3 are larger aluminum species. Peak 4 is smaller aluminum species (aluminum oligomers) and has been correlated with enhanced efficacy for both ACH and ZAG salts. Peak 5.6 is the smallest aluminum species. The relative retention time ("Kd") for each of these peaks varies depending on the experimental conditions.

In an illustrative embodiment, a solution of an oxo-hexameric zirconium-octaglycine salt, as described above, produced by the method of example 1 was analyzed by GPC. FIG. 3, shows the GPC chromatogram of the solution of example 1. It shows no eluting peak due to the small particle size of the oxo-hexameric zirconium-octaglycine complex in an conventional SEC profile, but it can be detected by a HPLC column or an appropriate SEC column. As evident from the SEC data of "ZG" salt, the present salt shows the absence of large and inefficacious zirconium species.

Example 4

Figure 4:
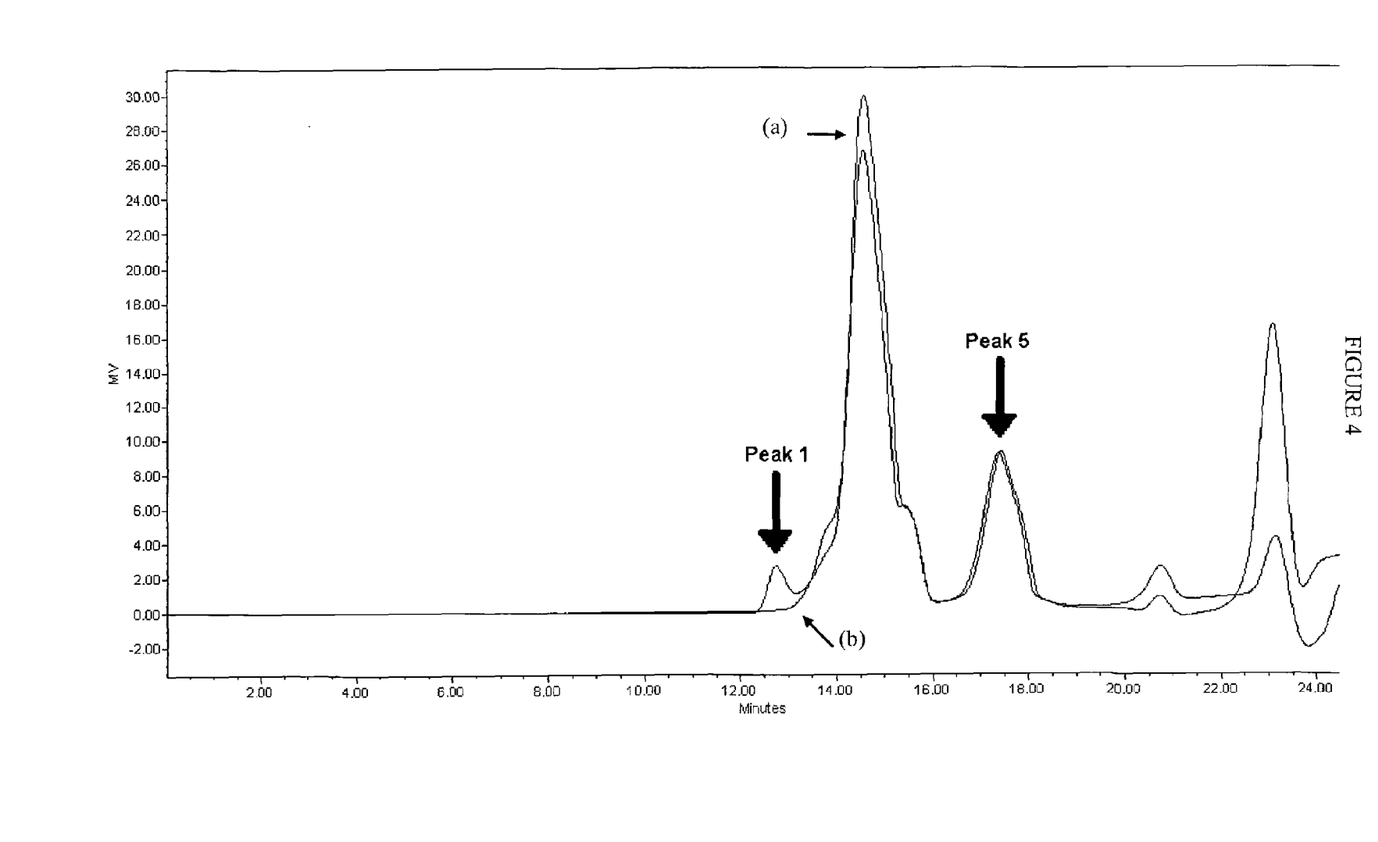
FIG. 4 is SEC chromatograms of (a) a solution of REACH™ 908 as compared to (b) a mixture of ACH 301 with oxo-$Zr_6Gly_8$ cluster cation.

The oxo-Zr6Gly8 complex (ZG) is mixed with REACH™ 301 aluminum chlorohydrate (ACH 301) to compare it to the current REACH™ AZP 908 ZAG species from Reheis. The addition of an inactive ACH 301 with ZG is compared to AZP 908 which also contains the same ACH species. FIG. 4 illustrates the advantage of the ACH 301+ZG compared to the standard AZP 908. These results reveal that no peak 1 can be detected after mixing the ZG with ACH 301 which is more favorable than using AZP 908 which produces a 3.28% peak 1. This demonstrates that no large Zr species are formed, which directly relates to an enhanced efficacy and increased AP stability. The ZG and ACH 301 are mixed into an aqueous solution at room temperature using 0.083 g ACH 301, 0.079 g ZG, and 0.84 g water. The Table below shows the peak values for the samples in FIG. 4.

| Sample | Line | Peak 1 | Peak 2 | Peak 3 | Peak 4 | Peak 5 |
|---|---|---|---|---|---|---|
| ACH 301 + ZG | (b) | 0.00% | 6.76% | 61.37% | 8.69% | 23.18% |
| AZP 908 | (a) | 3.28% | 4.62% | 64.72% | 6.92% | 20.46% |

Example 5

Figure 5:
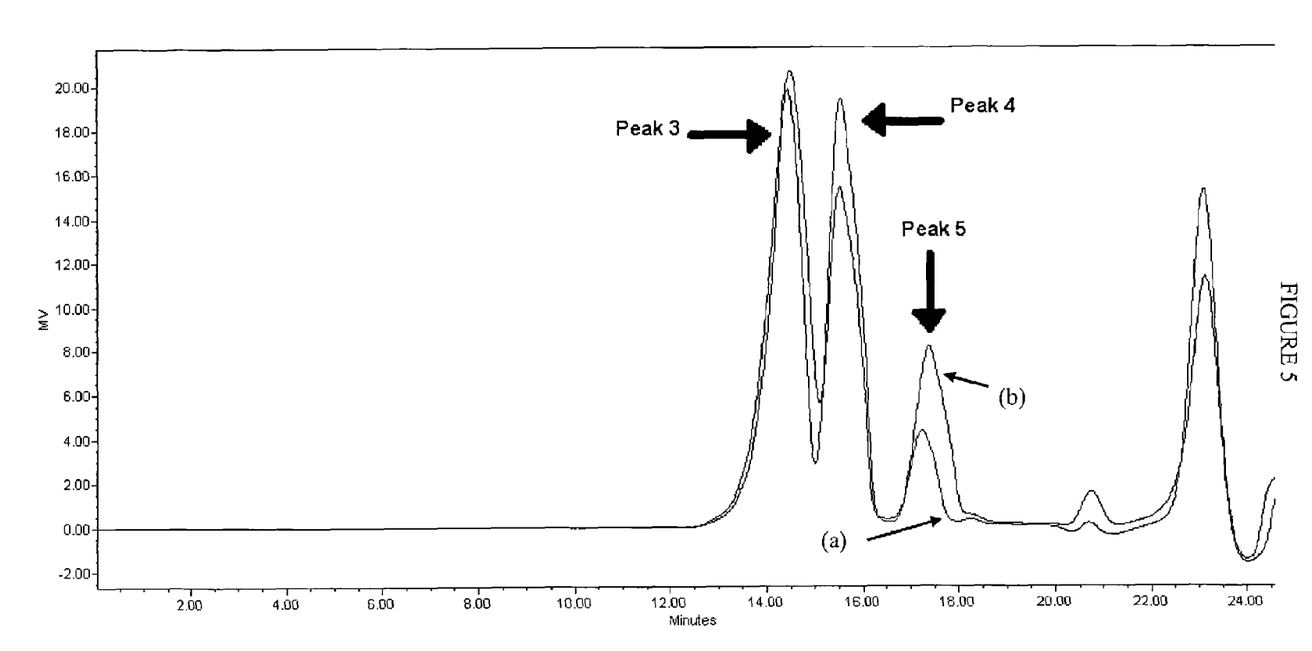
FIG. 5 is SEC chromatograms solutions of ACH 301 with oxo-$Zr_6Gly_8$ cluster cation (a) initially and (b) after 5 hours of aging.
Figure 6:
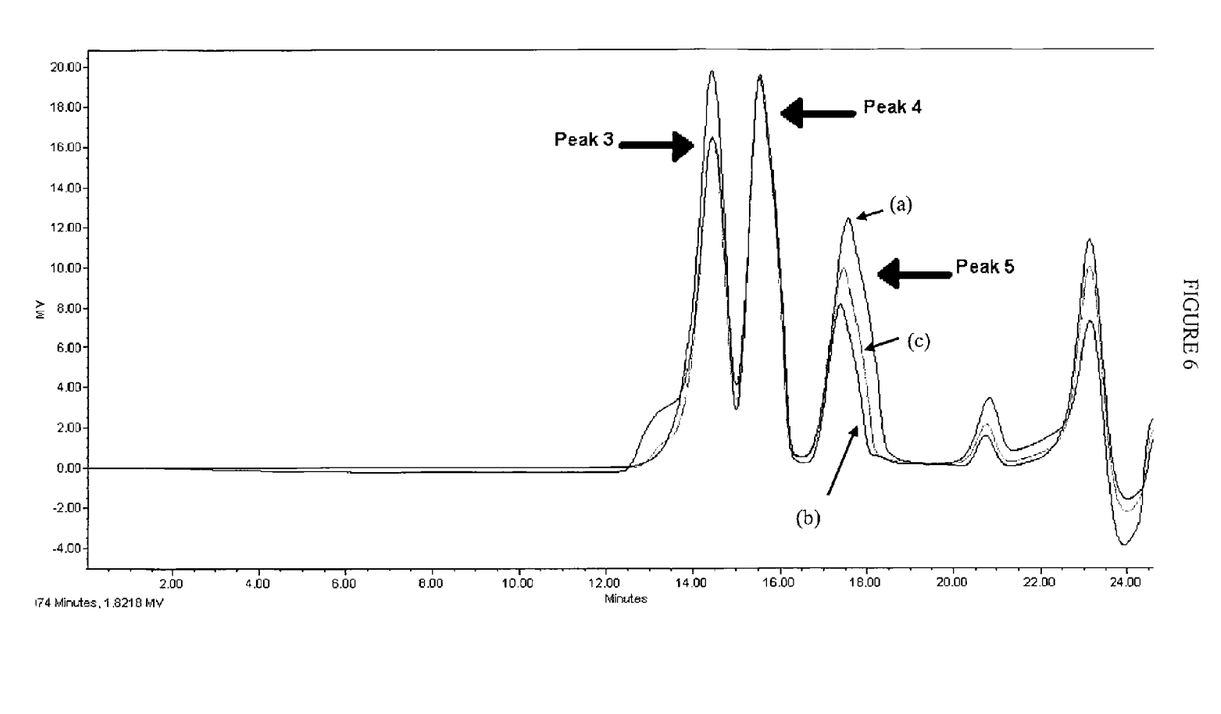
FIG. 6 is SEC chromatograms after 5 hours of aging for (a) AP4G, (b) mixture of ACH 301 with oxo-$Zr_6Gly_8$ cluster cation, and (c) SUMMIT™ Z576.

Initially when analyzing ACH 301+ZG, there was no peak 1, but the peak 4/peak 3 ratio was not as high as desired. A higher peak 4/peak 3 ratio is more advantageous for the production of an efficacious AP product. After allowing the sample to age for 5 hours, it was again analyzed using SEC. Upon aging for 5 hours, there was an increase in both peaks 4 and 5. FIG. 5 illustrates the advantage of allowing ACH 301+ZG to age for 5 hours. Upon aging, the ACH. 301+ZG has a comparable peak 4/peak 3 ratio along with a smaller peak 5 as seen in FIG. 6. These results reveal that no peak 1 can be detected after mixing the ZG hexamer with ACH 301. This demonstrates that no large Zr species are formed, which directly relates to enhanced efficacy and increased AP stability. Also, allowing ACH 301+ZG to age for 5 hours produces a more efficacious AP. Using the ACH 301+ZG is more advantageous than using Z376 and ZIRKONAL™ AP4G ZAG from BK Giulini because there are no large species produced. Also, there is a comparable peak 4/peak 3 ratio and a smaller peak 5 produced when using the ACH 301+ZG. The Tables below show the peak values for the samples in FIGS. 5 and 6, respectively.

| Sample | Line | Peak 1 | Peak 2 | Peak 3 | Peak 4 | Peak 5 |
|---|---|---|---|---|---|---|
| 5 hour aging | (b) | 0.00% | 0.00% | 43.98% | 39.28% | 16.74% |
| Unaged | (a) | 0.00% | 0.00% | 58.36% | 33.63% | 8.02% |

| Line | Line | Peak 1 | Peak 2 | Peak 3 | Peak 4 | Peak 5 |
|---|---|---|---|---|---|---|
| ACH 301 + ZG | (b) | 0.00% | 0.00% | 43.98% | 39.28% | 16.74% |
| AP4G | (a) | 0.00% | 6.49% | 30.20% | 34.83% | 28.48% |
| Z576 | (c) | 0.00% | 2.18% | 33.95% | 40.44% | 23.43% |

Example 6

Figure 7:
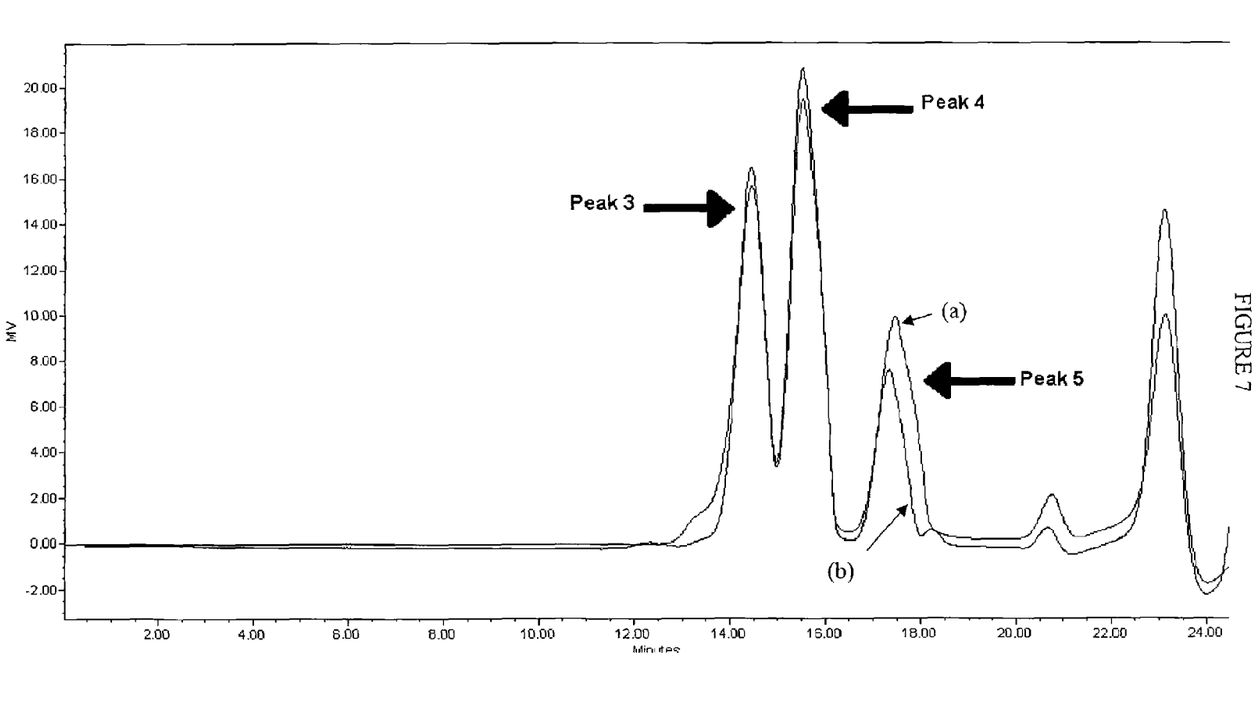
FIG. 7 is SEC chromatograms of (a) SUMMIT™ Z576 and (b) mixture of ACH 301 with oxo-$Zr_6Gly_8$ cluster cation.

A different ACH was tested to see if there were any differences as compared to ACH 301. In this example, REACH™ 103 (ACH 103) from Reheis (note: ACH 103 is a different product from ACH 301). The addition of the small oxo-$Zr_6Gly_8$ cluster (ZG) and ACH 103 was compared to the Z576 species. FIG. 7 shows that the ACH 103+ZG species is more advantageous than Z576. The ACH 103+ZG in FIG. 7 shows no peak 2 as well as a comparable peak 4/peak 3 ratio. The ACH 103+ZG also has a 7.20% decrease in peak 5. All of these results indicate that the ACH 103+ZG is a more efficacious AP product than Z576. These results reveal that no peak 1 can be detected after mixing the ZG hexamer with ACH 103. (The small peak 1 (0.55%) comes from the original ACH 103 sample). This demonstrates that no large Zr species are formed, which directly relates to enhanced efficacy and increased AP stability. The ZG and ACH 103 are mixed into an aqueous solution using 0.0805 g ACH 103, 0.074 g ZG, and 0.8476 g water. The Table below shows the peak values for the samples in FIG. 7.

| Line | Line | Peak 1 | Peak 2 | Peak 3 | Peak 4 | Peak 5 |
|---|---|---|---|---|---|---|
| ACH 103 + ZG | (b) | 0.55% | 0.00% | 35.38% | 47.84% | 16.23% |
| Z576 | (a) | 0.00% | 2.18% | 33.95% | 40.44% | 23.43% |

The above examples show that the addition of ZG to any aluminum chlorohydrate sample produced the same results with a more efficacious and stable antiperspirant product. There is an elimination of peaks 1 and 2 and a decrease in peak 5.

What is claimed is:

1. An oxo-hexameric zirconium-octaamino acid salt of the molecular formula:
   oxo-[$Zr_6AminoAcid_8$].Xy.n$H_2O$, wherein Zr is zirconium, X is an anion of a mineral acid, and n and y are independently numerical values of 0 to 20.

2. The oxo-hexameric zirconium-octaamino acid salt of claim 1, wherein X is at least one anion chosen from $Cl^-$, $SO_4^{2-}$, $NO_3^-$, $BO_3^{3-}$, $F^-$, $PO_4^{3-}$, and $ClO_4^-$.

3. The oxo-hexameric zirconium-octaamino acid salt of claim 1, wherein the amino acid is glycine.

4. The oxo-hexameric zirconium-octaamino acid salt of claim 3, wherein six zirconium atoms are located in an octahedral molecular geometry; wherein each adjacent three zirconium (Zr) atoms are capped by eight oxygen atoms to form a $Zr_6O_8$ core; and wherein each Zr is connected by a carboxylic group of a glycine as syn-syn mode to an apical Zr atom in the octahedral geometry.

5. An oxo-hexameric zirconium-octaglycine cluster cation comprising the following structure:

wherein zirconium is shown by diagonal lines running from upper left to lower right, oxygen is shown by diagonal lines running from lower left to upper right, nitrogen is shown by checkerboard, carbon is shown by solid white, hydrogen atoms on the carbon and nitrogen atoms to complete the valence for each atom are not shown, and wherein four oxygen atoms are shown with incomplete valences, which may be bonded to another structure or be completed with hydrogen atoms.

6. An oxo-hexameric zirconium-octaglycine cluster cation, wherein the X-ray powder diffraction exhibiting "d spacings" as measured using copper K-alpha radiation ($\lambda$=0.15046 nm) that are substantially as show below:

| Angle 2θ | d (Å) | I/$I_1$ |
|---|---|---|
| 7.37 | 11.98 | 100 |
| 7.95 | 11.10 | 30.33 |
| 8.77 | 10.08 | 70.72 |
| 10.43 | 8.47 | 50.38 |
| 10.85 | 8.15 | 10.99 |
| 16.53 | 5.36 | 9.93. |

7. The oxo-hexameric-zirconium-octaamino acid salt of claim 1 further comprising aluminum chlorohydrate.

8. An oxo-hexameric zirconium-octaglycine cluster cation of claim 5 further comprising aluminum chlorohydrate.

9. The oxo-hexameric-zirconium-octaglycine cluster cation of claim 6 further comprising aluminum chlorohydrate.

10. A process for preparing an oxo-hexameric zirconium-octaamino acid salt comprising:
   a) mixing zirconium (Zr):amino acid:and mineral acid (MA) in a molar ratio of 1:about 1 to about 15:about 1.5 to about 3 to form a mixture;
   b) optionally, filtering the mixture; and
   c) optionally, drying the mixture.

11. The process of claim 10, wherein the amino acid is at least one amino acid chosen from glycine, alanine, threonine, leucine, tryptophan, phenylalanine, valine, and methionine.

12. The process of claim 10, wherein the mineral acid comprises at least one mineral acid chosen from sulfuric acid, hydrochloric acid, nitric acid, hydrobromic acid, phosphoric acid, boric acid, hydrofluoric acid, and perchloric acid.

13. The process of claim 10, wherein the molar ratio is 1:about 8 to about 12:about 1.5 to about 3.

14. The process of claim 10, wherein the a molar ratio 1:about 10:about 2.

15. The process of claim 10, wherein amino acid is glycine and the molar ratio is 1:about 10:about 2.

16. The oxo-hexameric zirconium-octaamino acid salt prepared according to the process of claim 10.

17. The oxo-hexameric zirconium-octaamino acid salt prepared according to the process of claim 15.

18. The process of claim 10, wherein the amino acid is glycine and the molecular ratio of glycine to zirconium (Gly/Zr) is at least about 1.3.

19. A method of making an antiperspirant active zirconium-aluminum-amino acid compound comprising the steps of:
   a) mixing an oxo-hexameric zirconium-octaamino acid salt in an aqueous solution;
   b) admixing aluminum chlorohydrex (ACH) and/or aluminum chloride ($AlCl_3$) into the oxo-hexameric zirconium-octaamino acid salt solution to form a mixture;
   c) drying the mixture to obtain the zirconium-aluminum-amino acid salt;
   wherein a molar ratio of zirconium-amino acid to ACH and/or $AlCl_3$ is 1:about 1.2 to about 1:5.

20. The method of claim 19, wherein the amino acid is glycine.

21. The method of claim 19, wherein the oxo-hexameric zirconium-octaamino acid salt is prepared by a process comprising:
   a) mixing zirconium (Zr):amino acid:and mineral acid (MA) in a molar ratio of 1:about 1 to about 15:about 1.5 to about 3 to form a mixture;
   b) optionally, filtering the mixture; and
   c) optionally, drying the mixture.

22. The method of claim 19, wherein the oxo-hexameric zirconium-octaamino acid salt is prepared by a process comprising:
   a) mixing zirconium (Zr):glycine:and mineral acid (MA) in a molar ratio of 1:about 10:about 2 to form a mixture;
   b) optionally, filtering the mixture; and
   c) optionally, drying the mixture.

23. The method of claim 19, wherein the oxo-hexameric zirconium-octaamino acid salt has a structure comprising: oxo-[$Zr_6$AminoAcid$_8$].Xy.$nH_2O$, wherein Zr is zirconium, X is an anion of a mineral acid, and n and y are independently numerical values of 0 to 20.

24. The method of claim 19, wherein the oxo-hexameric zirconium-octaamino acid salt contains an oxo-hexameric zirconium-octaglycine cluster cation comprising the following structure:

wherein zirconium is shown by diagonal lines running from upper left to lower right, oxygen is shown by diagonal lines running from lower left to upper right, nitrogen is shown by checkerboard, carbon is shown by solid white, hydrogen atoms on the carbon and nitrogen atoms to complete the valence for each atom are not shown, and wherein four oxygen atoms are shown with incomplete valences, which may be bonded to another structure or be completed with hydrogen atoms.

25. The method of claim 19, wherein, wherein the oxo-hexameric zirconium-octaamino acid salt comprises an oxo-hexameric zirconium-octaglycine cluster cation, wherein the X-ray powder diffraction exhibiting "d spacings" as measured using copper K-alpha radiation ($\lambda$=0.15046 nm) that are substantially as show below:

| Angle 2θ | d (Å) | $I/I_1$ |
| --- | --- | --- |
| 7.37 | 11.98 | 100 |
| 7.95 | 11.10 | 30.33 |
| 8.77 | 10.08 | 70.72 |
| 10.43 | 8.47 | 50.38 |
| 10.85 | 8.15 | 10.99 |
| 16.53 | 5.36 | 9.93. |

* * * * *